United States Patent
Park et al.

[11] Patent Number: 5,866,800
[45] Date of Patent: Feb. 2, 1999

[54] GAS SENSOR AND METHOD FOR FABRICATING SAME

[75] Inventors: Hyeon Soo Park; Hyun Woo Shin; Chul Han Kwon; Hyung Ki Hong; Dong Hyun Yun; Kyuchung Lee; Sung Tae Kim, all of Seoul, Rep. of Korea

[73] Assignee: LG Semicon Co., Ltd., Chungcheongbuk-Do, Rep. of Korea

[21] Appl. No.: 548,387

[22] Filed: Oct. 26, 1995

[30] Foreign Application Priority Data

Oct. 26, 1994 [KR] Rep. of Korea .......... 27489/1994

[51] Int. Cl.⁶ .......... G01N 27/12; G01N 27/26
[52] U.S. Cl. .......... 73/31.06; 73/23.31; 73/29.01; 422/83
[58] Field of Search .......... 73/31.05, 31.06, 73/30.04, 23.31, 29.01; 422/83

[56] References Cited

U.S. PATENT DOCUMENTS

| | | | |
|---|---|---|---|
| 4,223,550 | 9/1980 | Takahama et al. | 73/23 |
| 4,343,768 | 8/1982 | Kimura | 422/97 |
| 4,377,944 | 3/1983 | Hishii et al. | 73/23 |
| 4,413,502 | 11/1983 | Ohta et al. | 73/23 |
| 4,697,165 | 9/1987 | Ishiguro et al. | 33/34 |
| 4,822,465 | 4/1989 | Jones et al. | 204/192.1 |
| 5,367,283 | 11/1994 | Lauf et al. | 338/34 |
| 5,591,896 | 1/1997 | Lin | 73/31.05 |
| 5,605,612 | 2/1997 | Park et al. | 204/429 |
| 5,659,127 | 8/1997 | Shie et al. | 73/31.05 |
| 5,698,771 | 12/1997 | Shields et al. | 73/31.05 |

*Primary Examiner*—Michael Brock
*Assistant Examiner*—J. David Wiggins
*Attorney, Agent, or Firm*—Morgan, Lewis & Bockius LLP

[57] ABSTRACT

A gas sensor and a method for fabricating the same includes a semiconductor substrate, a supporting layer formed on the semiconductor substrate, the supporting layer being electrically insulative and having a pattern groove formed therein, a heater formed in the pattern groove, an electrically insulating layer formed on the heater and the supporting layer, an electrode formed on the insulating layer, and a sensing layer formed on the electrode and the insulating layer to detect a target gas of interest according to a measured change in electrical conductivity or resistance thereof.

12 Claims, 5 Drawing Sheets

GAS SENSOR AND METHOD FOR FABRICATING SAME

BACKGROUND OF THE INVENTION

1. Field of the Invention

The present invention relates to a gas sensor and a method for fabricating the same, and more particularly, to a gas sensor having a built-in micro heater and a method for fabricating the same.

2. Discussion of the Related Art

In various applications, a gas sensor detects gas leakage, oxygen deficiency, and pollution materials made of nitrogen or carbon oxide. In addition, gas sensors control combustion conditions in engines and boilers.

A conventional semiconductor gas sensor, used in applications as described above, usually comprises a gas sensing portion, a heater portion, and an explosion-proof net. The operation of this gas sensor will now be explained.

First, when gas contacts a sensing layer, charge transfer occurs between gas molecules and the sensing layer, thereby changing the electrical conductivity of the sensing layer, i.e., the resistance. The electrical current passing through the electrodes is correspondingly changed. In this manner, the presence of gas is detected.

When a current flows through the heater, the gas sensing layer is heated by the heater. This improves the sensitivity and responsivity of the sensing layer, while also removing contaminants from the sensing layer.

According to a general method not employing semiconductor technology, the heater having the aforementioned performance is embodied in the form of coil of metal lines of Ni—Cr, Ta or Pt, as shown in FIG. 1. The coil-type heater is primarily used to heat ceramic tubes. However, the coil-type, heater is not available for integrated devices such as flat-type sensors.

In order to overcome the drawbacks of the coil-type heater, a thick film-type heater has been proposed which heats a ceramic substrate using a heater pattern formed in screen printing. The gas sensor having the thick film-type heater made with screen printing will now be explained with reference to FIGS. 1 to 3.

FIG. 1 is a plan view of a conventional thick film-type heater. FIG. 2 is a cross-sectional view of a conventional gas sensor having the thick film-type-heater shown in FIG. 1.

As shown in FIG. 1, a, screen in which a heater pattern 4 is formed on a ceramic substrate 1, and the screens are spaced at predetermined intervals. Then, printing is carried out using a paste of the heater material, such as Pt or $RuO_2$ paste. Next, heat treatment of ceramic substrate 1 is performed at a high temperature, thereby removing organic materials in the paste. As a result, only the heater material of Pt or $RuO_2$ remains on ceramic substrate 1 in the form of the heater pattern, thereby completing the heater.

As shown in FIG. 2, a conventional gas sensor consists of a ceramic substrate 1, an electrode 2 formed on the overall surface of the ceramic substrate 1, a sensing layer 3 formed on the overall surface of the electrode 2, and a thick film-type heater 4 formed on the back of the ceramic substrate 1.

However, in this conventional gas sensor, the thick film-type heater 4 formed by the screen printing method is too thick, i.e., greater than tens of micrometers, to fabricate fine patterns. In addition, the thick film-type heater increases the consumption of power, and is difficult to apply to semiconductor fabricating technology.

Meanwhile, wet etching and dry etching has also been used to form the heater pattern. The process of forming the heater pattern using etching will now be explained.

A heater material such as Pt or Au is deposited on a supporting layer, and the heater material formed on undesired portions is etched using photolithography, thereby finishing the heater pattern. However, the etching method as described above complicates the process because an etchant is used. The metal (such as Pt or Au) is difficult to etch, thereby preventing accurate etching.

Accordingly, a lift-off method has become widely used because a separate etch solution is not required in the heater pattern formation process, and a material difficult to etch can be selectively removed, for example, Pt or Au. The lift-off method will now be briefly described.

First, a photoresist is coated on a supporting layer, and the photoresist is selectively removed using photolithography to expose a portion of the supporting layer where a heater material is desired and to leave the photoresist on a portion of the supporting layer where a heater material is not desired.

Then, heater material is deposited on the supporting layer and photoresist, and the resulting structure is dipped in acetone to dissolve the photoresist using ultrasound. As a result, the photoresist and the heater-material deposited on the photoresist is removed, leaving the heater material only on the heater pattern where the supporting layer is exposed.

Recently, a method for fabricating a micro heater having a small structure through the aforementioned lift-off method using semiconductor technology has been proposed. This technology will now be briefly explained with reference to FIGS. 3a to 3d.

FIGS. 3a and 3d are cross-sectional views of the sequential manufacturing process of a conventional method for fabricating a heater of a gas sensor using the lift-off method.

As shown in FIG. 3a, a silicon oxide or silicon nitride is grown on a silicon substrate (not shown) to form a supporting layer 12. Photoresist 13 is coated on the supporting layer 12, and, as shown in FIG. 3b, and selectively etched leaving the photoresist only where a heater material, which will be deposited in the following step, will not be required. Through this process, a heater pattern 13a is formed. Here, the upper edge of the remaining photoresist is made with an overhang A. The purpose for the heater pattern 13a formed with the photoresist overhang A will be described below.

In the conventional manufacturing process of the gas sensor, photoresist is coated on the supporting layer, and then the photoresist is vertically etched to be left only on a portion where the heater material is not required, forming the heater pattern. The heater material is deposited on the overall surface of the heater pattern, and the heater pattern, which is left in the unrequired portion, is removed using the lift-off process. Here, the heater material comes into contact with the side of the heater pattern, whose side is not etched and is left without change during the photoresist etch process. Accordingly, the heater pattern of the unrequired portion is not perfectly removed.

Therefore, when the upper edge of the heater pattern has the overhang structure, the heater material does not make contact with the side of the heater pattern.

Then, as shown in FIG. 3c, a heater material 14 is deposited on the overall surface of the supporting layer 12, and the resulting structure is dipped in acetone and the heater pattern 13a is dissolved in the acetone using ultrasound. At this time, the heater material 14 on the heater pattern 13a is removed as the heater pattern 13a is removed. The heater material 14 is left only on the heater pattern portion where the supporting layer 12 is exposed, thereby completing the heater 14a.

However, as shown in FIG. 3b, even if the photoresist 13 is patterned in such a manner that its upper edge has overhang structure A, the heater material 14 is deposited on the supporting layer 12 by falling down on the heater pattern 13a not vertically but at various angles. As a result, the heater material is deposited even on the lower side of the overhang structure so that both ends of the heater material are higher than the center. Therefore, as shown in FIG. 3d, an undesired blade-shaped vertical pattern B is formed on the sides of the heater 14a.

If the semiconductor gas sensor is manufactured as the aforementioned heater, an insulation layer formed between the heater and electrode is so thin that the blade-shaped vertical pattern formed on both sides of the heater, may undesirably come into contact with the electrode. Accordingly, insulation between the heater and electrode is destroyed, thereby deteriorating the characteristics of the gas sensor.

SUMMARY OF THE INVENTION

Accordingly, the present invention is directed to a gas sensor that substantially obviates one or more of the problems due to limitations and disadvantages of the related art.

An object of the present invention is the provision of a gas sensor and a method of fabricating the same which increases the insulation between a heater and electrode, thereby improving the reliability of the gas sensor.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purpose of the present invention, as embodied and broadly described, the gas sensor includes a semiconductor substrate, a supporting layer formed on the semiconductor substrate, the supporting layer having a pattern groove formed therein, a heater formed in the pattern groove, an insulating layer formed on the heater and the supporting layer, an electrode formed on the insulating layer, and a sensing layer formed on the electrode and the insulating layer.

In another aspect, the method for fabricating a gas sensor includes the steps of forming a supporting layer on a semiconductor substrate, forming a pattern groove on the supporting layer, forming a heater in the pattern groove, forming an insulating layer on the heater and the insulating layer, forming an electrode on the insulating layer, and forming a sensing layer on the electrode and the insulating layer.

To further accomplish the objects of the present invention, the gas sensor includes a semiconductor substrate with a back etched to a predetermined portion, a supporting layer formed on the semiconductor substrate and having a pattern groove thereon, a heater formed on the pattern groove, an insulating layer formed on the overall surface of the heater, an electrode formed on the insulating layer, and a sensing layer formed on the overall surface of the electrode.

In yet another aspect, the method of fabricating a gas sensor includes the steps of preparing a semiconductor substrate, forming a supporting layer consisting of upper and lower supporting layers on the semiconductor substrate, forming a pattern groove on the supporting layer, forming a heater on the pattern groove, forming an insulating layer on the overall surface of the heater, forming an electrode on the insulating layer, forming a sensing layer on the overall surface of the electrode, and etching the back of the semiconductor substrate to expose the lower supporting layer.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention. In the drawings.

DETAILED DESCRIPTION OF THE PREFERRED EMBODIMENTS

Reference will now be made in detail to the preferred embodiments of the present invention, examples of which are illustrated in the accompanying drawings.

Figure 1:
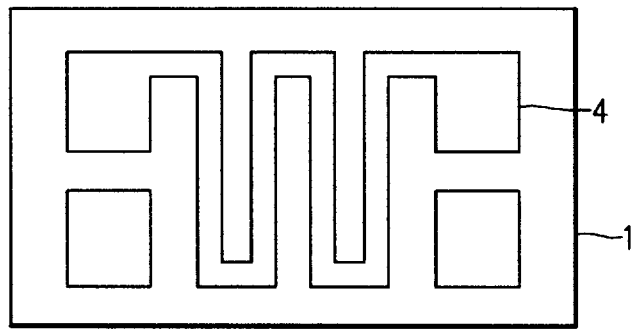
FIG. 1 is a plan view of a conventional thick film-type heater.
Figure 2:
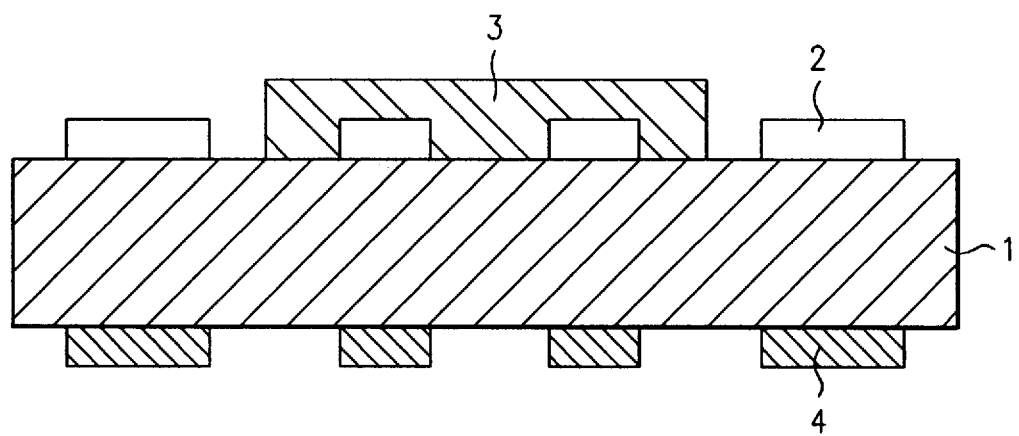
FIG. 2 is a cross-sectional view of a conventional gas sensor with the thick film-type heater of FIG. 1.
Figure 3A:
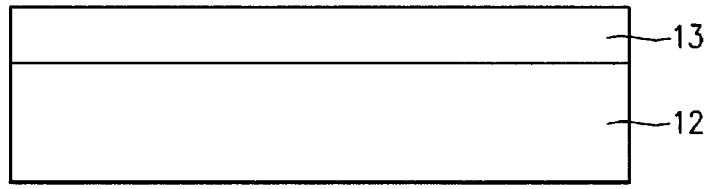
FIGS. 3a to 3d are cross-sectional views of the manufacturing process of a conventional method for fabricating a heater of a gas sensor.
Figure 3B:
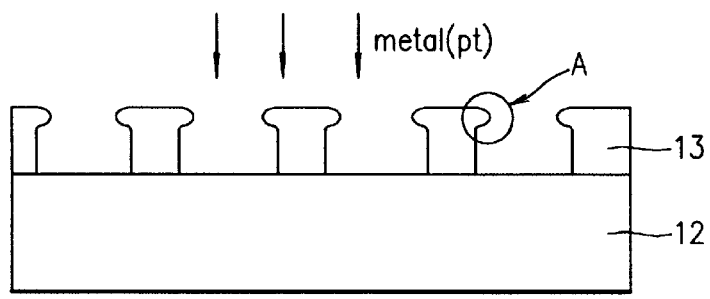
Figure 3C:
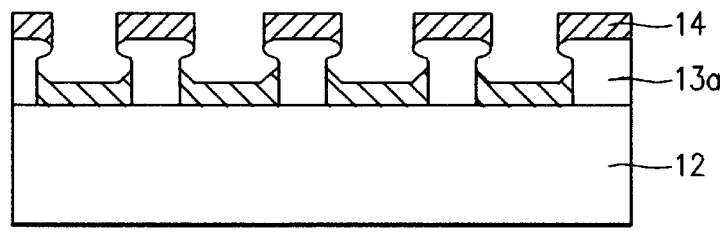
Figure 3D:
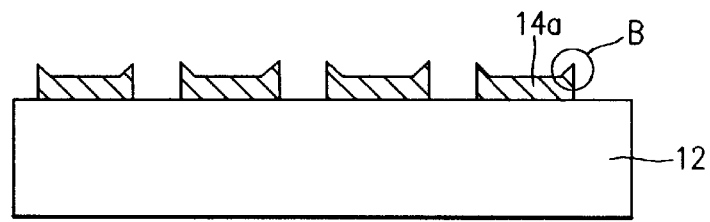
Figure 4:
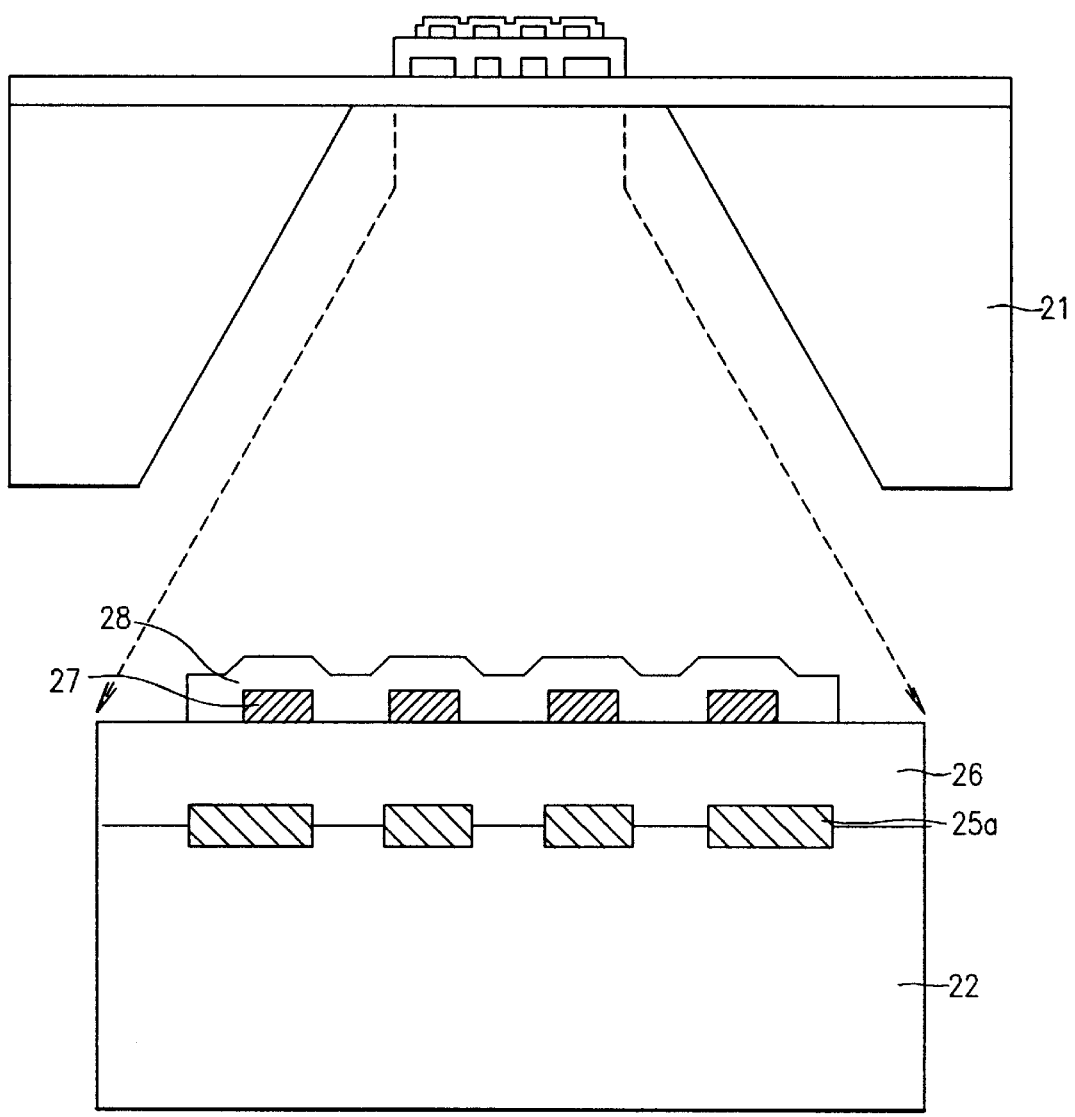
FIG. 4 is a cross-sectional view of a gas sensor in accordance with the present invention.
Figure 5A:
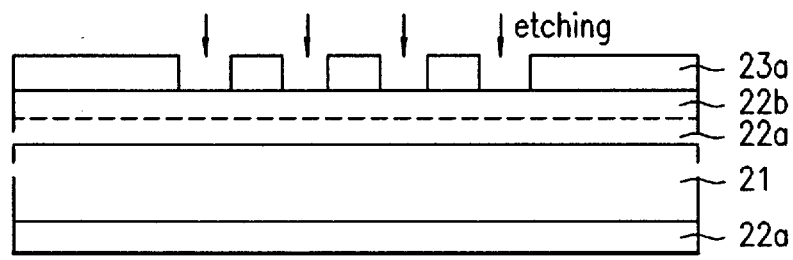
FIGS. 5a to 5f are cross-sectional views of a manufacturing process of a method for fabricating a gas sensor according to the present invention.

FIG. 4 is a cross-sectional view of a gas sensor in accordance with the present invention. As shown in FIG. 4, a gas sensor according to the present invention includes a semiconductor substrate 21 whose back surface is etched to a predetermined portion, a supporting layer 22 formed on the semiconductor substrate 21 and having a pattern groove 24, a heater 25a formed on the pattern groove 24, and insulating layer 26 formed on the overall surface of the heater 25a, an electrode 27 formed on the insulating layer 26, and a sensing layer 28 formed on the overall surface of the electrode 27. Here, the supporting layer 22 includes a lower supporting layer 22a and upper supporting layer 22b as shown in FIG. 5a. For example, the lower supporting layer 22a is formed of silicon nitride, and the upper supporting 22b is formed of phosphosilicate glass (PSG). The lower and upper supporting layer 22a and 22b can be formed of insulating materials besides silicon nitride and PSG.

A method of fabricating the gas sensor having the aforementioned structure will now be explained with reference to the accompanying drawings. FIGS. 5a to 5f are cross-sectional views of the sequential manufacturing processes of a method for fabricating a gas sensor according to the present invention.

First, a semiconductor substrate 21, for example, a p-type wafer with both sides polished, is prepared. Then, a standard cleaning process using acetone,. methanol, and deionized water is performed. A native oxide formed on the surface of the semiconductor substrate 21 is removed using fluoric acid.

As shown in FIG. 5a, an insulating material, for example, silicon nitride thousands of Å thick is deposited on the top and bottom of the semiconductor substrate 21 to form a lower supporting layer 22a. The lower supporting layer 22a will stop etching and support other structures. Here, the silicon nitride is deposited at a temperature of about 800° with $SiH_2Cl_2$ gas and $NH_3$ gas using low pressure chemical vapor deposition (LPCVD).

Next, an insulating material, such as PSG, is deposited to thousands or tens of thousand of Å thick on the front surface of the semiconductor substrate 21 over the lower supporting layer 22a, to form a upper supporting layer 22b. Consequently, a double-structured supporting layer 22 of the lower and upper supporting layers 22a and 22b is formed with differing etching characteristics. Preferably, a material easy to etch and having an excellent thermal isolation and mechanical strength can be applied for the insulating material of upper supporting layer 22b, such as PSG. The PSG is deposited at a temperature of about 450° with $SiH_4$, $PH_3$ and $O_2$ gas using atmospheric pressure chemical vapor deposition (APCVD).

Then, the substrate is cleaned and coated with hexamethyldisilazane (HMDS; $<CH_3>_3SiNHSi<CH_3>_3$), an organic silane, to improve adhesion of photoresist. Photoresist is coated on the substrate, and kept at about 90° C. for 20 minutes. Sequential exposure and developing processes are performed to form a heater pattern 23a.

Figure 5B:
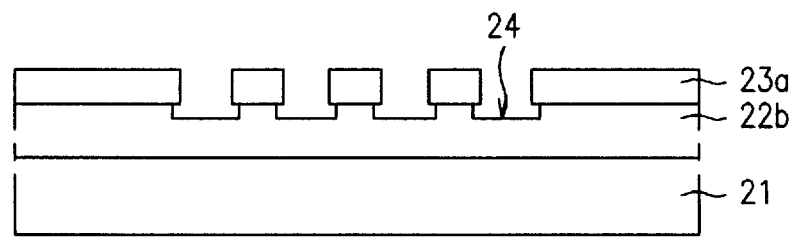

As shown in FIG. 5b, a upper portion of the supporting layer 22 in which the heater pattern is formed, is etched to a predetermined depth, to form a pattern groove 24. At this time, the upper edge of the etched supporting layer 22 and the lower edge of the heater pattern 23a are made to have an overhang.

Figure 5C:
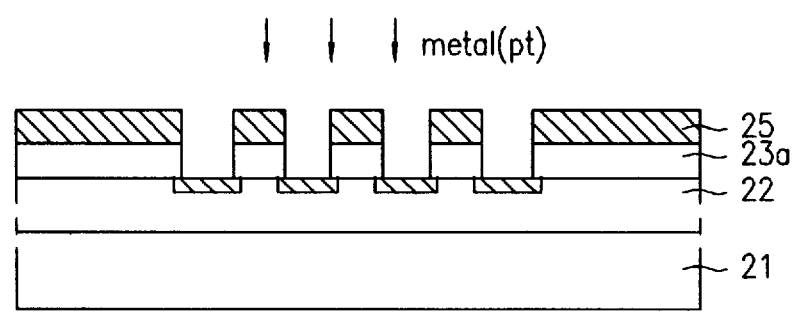

As shown in FIG. 5c, a heater material 25, for example, Pt, is deposited on the supporting layer 22 in the pattern groove 24. Here, Pt is sputtered because Pt is stable and has a very high melting point. A Ti layer of hundreds of Å can be formed between the heater material 25 and the supporting layer 22 to improve adhesion between them.

At this time, the supporting layer 22 of the present invention has been selectively etched, on which the heater material 25 is deposited, to a predetermined depth so that the (blade-shaped) vertical pattern of the heater material cannot rise higher than supporting layer 22.

Figure 5D:
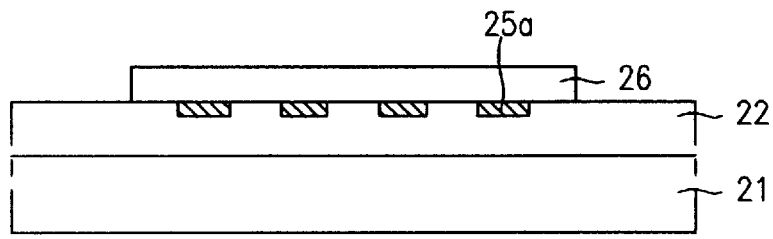

As shown in FIG. 5d, the heater pattern 23a is removed using the lift-off process. Here, the heater material 25 formed on the heater pattern 23a is removed with the heater pattern 23a. Then, an insulating material such as a silicon nitride is deposited on the overall surface of the substrate, thereby forming an insulating layer 26.

Figure 5E:
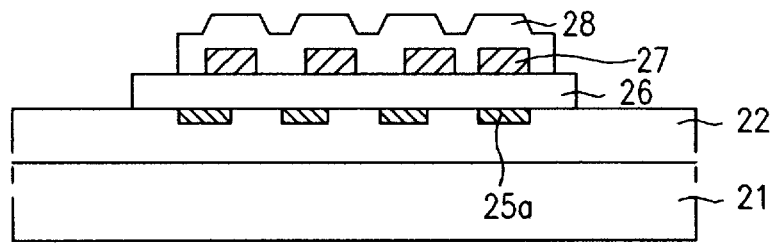

As shown in FIG. 5e, the insulating layer 26 is selectively etched to form a contact hole (not shown), and an electrode 27 is formed in the contact hole. Next, a metal oxide is coated on the overall surface of the electrode 27 to form the gas sensing layer 28.

Figure 5F:
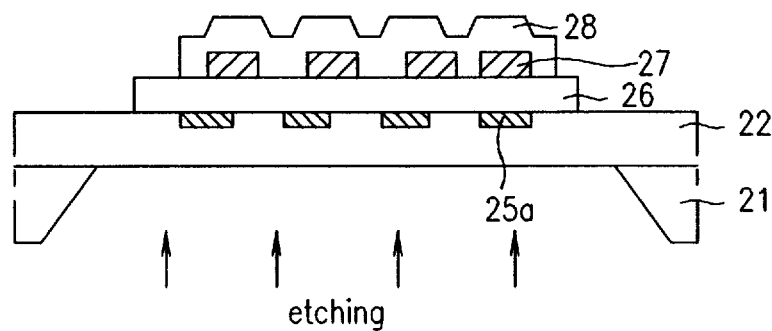

As shown in FIG. 5f, after finishing the front surface of the substrate, the silicon nitride, that is, the lower supporting layer 22a located on the lower portion of the substrate, is dry-etched, to form an etching window. Then, anisotropic etching with a KOH solution is performed for several hours until the silicon nitride of the lower supporting layer 22a formed on the front surface of the substrate 21 is exposed. When the etching of the back of the substrate is finished, the gas sensor having a back structure is completed.

In the present invention, the upper portion of the supporting layer where the heater is formed is etched to a predetermined depth so as to prevent the blade-shaped vertical pattern, which is formed on both sides of the upper portion of the heater, from becoming higher than the supporting layer. This maintains a stable insulation distance between the heater and electrode so that secure insulation between the heater and electrode is guaranteed.

Therefore, the gas sensor in accordance with the present invention has highly reliable insulation effect even if the gas sensor is operating at high temperatures for extended periods.

It will be apparent to those skilled in the art that various modifications and variations can be made in the gas sensor of the present invention without departing from the spirit or scope of the invention. Thus, it is intended that the present invention cover the modifications and variations of this invention provided they come within the scope of the appended claims and their equivalents.

What is claimed is:

1. A gas sensor comprising:
    a semiconductor substrate;
    a supporting layer formed on the semiconductor substrate, the supporting layer being electrically insulative and having a pattern groove formed therein;
    a heater formed in the pattern groove;
    an electrically insulating layer formed on the heater and the supporting layer;
    an electrode formed on the insulating layer; and
    a sensing layer formed on the electrode and the insulating layer to detect a target gas of interest according to a measured change in electrical conductivity or resistance thereof.

2. The gas sensor according to claim 1, wherein the semiconductor substrate has a back surface which is etched in a predetermined portion.

3. The gas sensor according to claim 1, wherein a portion of the semiconductor substrate is removed to expose the supporting layer.

4. The gas sensor according to claim 1, wherein the pattern groove is formed on the surface of the supporting layer as deep as an edge of the heater.

5. The a gas sensor according to claim 1, wherein the heater remains below an upper surface of the supporting layer.

6. The gas sensor according to claim 1, wherein an etching rate of an upper portion of the supporting layer is different than an etching rate of a lower portion of the supporting layer.

7. The gas sensor according to claim 6, wherein an etching rate of the upper portion is greater than an etching rate of the lower portion.

8. The gas sensor according to claim 6, wherein the upper portion is formed of phosphosilicate glass (PSG) and the lower portion is formed of silicon nitride.

9. The gas sensor according to claim 6, wherein the semiconductor substrate has a back surface which is etched in a predetermined portion.

10. The gas sensor according to claim 6, wherein a portion of the semiconductor substrate is removed to expose the supporting layer.

11. The gas sensor according to claim 6, wherein the pattern groove is formed on the surface of the supporting layer as deep as an edge of the heater.

12. The a gas sensor according to claim 6, wherein the heater remains below an upper surface of the supporting layer.

* * * * *